(12) United States Patent
Ooms et al.

(10) Patent No.: US 8,882,984 B2
(45) Date of Patent: Nov. 11, 2014

(54) PROCESS FOR PREPARING DIARYL CARBONATE

(75) Inventors: Pieter Ooms, Krefeld (DE); Andreas Bulan, Langenfeld (DE); Johann Rechner, Kempen (DE); Rainer Weber, Odenthal (DE); Michael Traving, Burscheid (DE); Marc Buts, Duffel (BE); Johan Vanden Eynde, Zwijnaarde (BE)

(73) Assignee: Bayer MaerialScience AG, Leverkusen (DE)

( * ) Notice: Subject to any disclaimer, the term of this patent is extended or adjusted under 35 U.S.C. 154(b) by 528 days.

(21) Appl. No.: 12/759,074

(22) Filed: Apr. 13, 2010

(65) Prior Publication Data
US 2010/0286431 A1 Nov. 11, 2010

(30) Foreign Application Priority Data
Apr. 17, 2009 (DE) .......................... 10 2009 017 862

(51) Int. Cl.
*C07C 69/96* (2006.01)
*C01D 3/04* (2006.01)
*C07C 68/02* (2006.01)

(52) U.S. Cl.
CPC .. *C01D 3/04* (2013.01); *C07C 68/02* (2013.01)
USPC ............................ 205/338; 205/439; 558/274

(58) Field of Classification Search
None
See application file for complete search history.

(56) References Cited

U.S. PATENT DOCUMENTS

| | | | |
|---|---|---|---|
| 3,773,634 A | 11/1973 | Stacey et al. | |
| 4,016,190 A | 4/1977 | Böckmann et al. | |
| 4,025,405 A | 5/1977 | Dotson et al. | |
| 5,340,905 A | 8/1994 | Kühling et al. | |
| 5,734,004 A | 3/1998 | Kühling et al. | |
| 6,340,736 B1 * | 1/2002 | Coenen et al. | 528/196 |
| 6,531,623 B2 | 3/2003 | Chrisochoou et al. | |
| 6,548,691 B2 | 4/2003 | Alewelt et al. | |
| 6,680,400 B2 * | 1/2004 | Alewelt et al. | 558/274 |
| 2005/0115901 A1 | 6/2005 | Heuser et al. | |
| 2008/0053836 A1 | 3/2008 | Bulan et al. | |

FOREIGN PATENT DOCUMENTS

| | | |
|---|---|---|
| CA | 2375245 A1 | 12/2000 |
| DE | 102006041465 A1 | 3/2008 |
| EP | 541114 A2 | 5/1993 |
| EP | 0784048 A1 | 7/1997 |
| EP | 1216981 A2 | 6/2002 |
| EP | 1216982 A2 | 6/2002 |
| EP | 1219589 A1 | 7/2002 |
| EP | 1200359 B1 | 2/2004 |
| EP | 1894914 A2 | 3/2008 |
| WO | WO-00/78682 A1 | 12/2000 |
| WO | WO-01/38419 A1 | 5/2001 |
| WO | WO-03/070639 A1 | 8/2003 |

OTHER PUBLICATIONS

Chapter 6. Membrane distillation and osmotic distillation, In: Enrico Drioli, Alessandra Criscuoli and Efrem Curcio, Editor(s), Membrane Science and Technology, Elsevier, 2005, vol. 11, pp. 186-253. (http://www.sciencedirect.com/science/article/pii/S0927519305800075) Accessed Jan. 25, 2012.*

* cited by examiner

*Primary Examiner* — Alicia L Otton
(74) *Attorney, Agent, or Firm* — Drinker Biddle & Reath LLP

(57) ABSTRACT

A process for preparing diaryl carbonate and utilizing at least part of the process wastewater by increasing the concentration of the wastewater phases containing sodium chloride for the electrolysis by means of osmotic membrane distillation with simultaneous dilution of the sodium hydroxide solution obtained from the electrolysis for the diaryl carbonate production process (diphenyl carbonate process) is described.

19 Claims, 1 Drawing Sheet

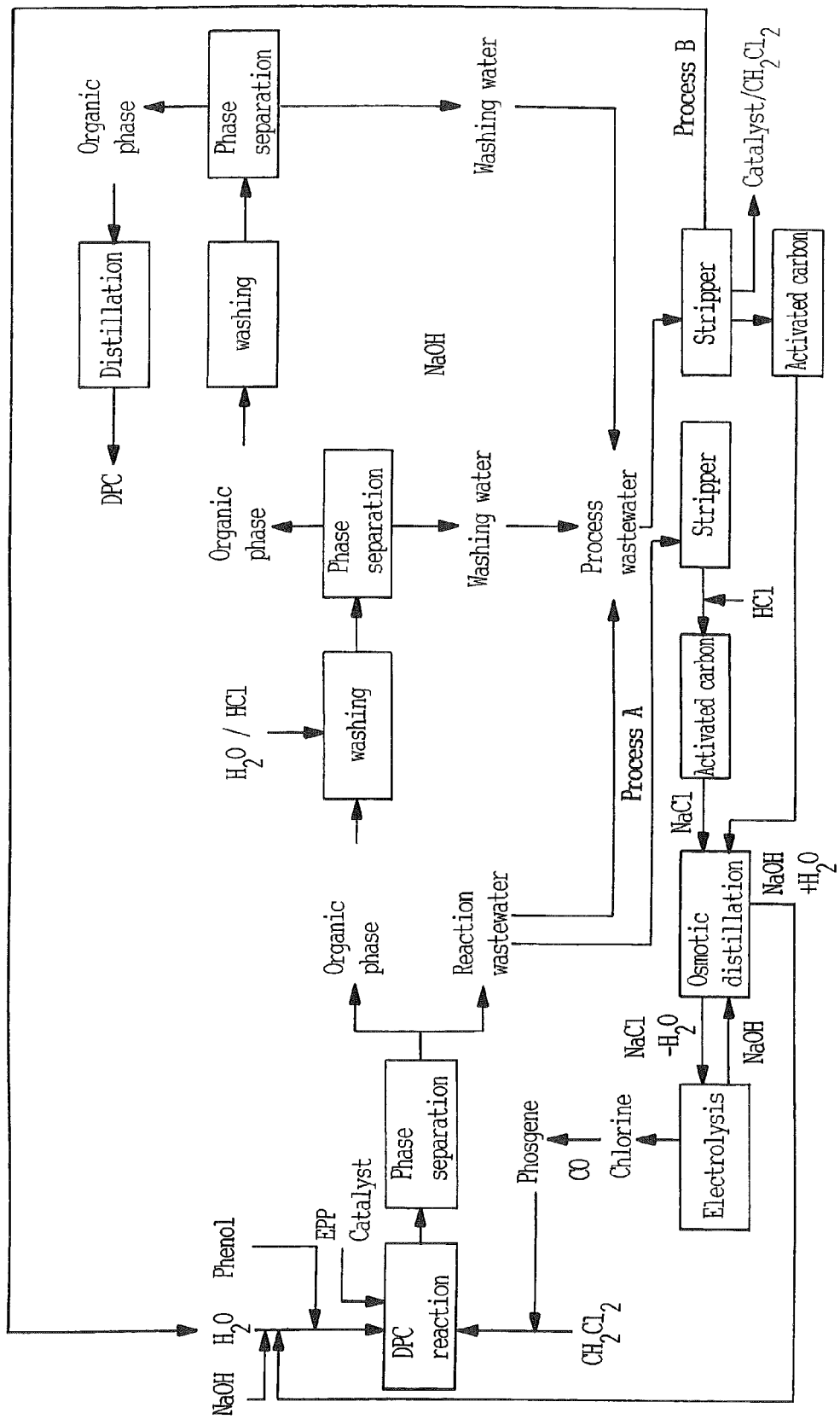

PROCESS FOR PREPARING DIARYL CARBONATE

RELATED APPLICATIONS

This application claims benefit to German Patent Application. No. 10 2009 017 862.7, filed Apr. 17, 2009, which is incorporated herein by reference in its entirety for all useful purposes.

BACKGROUND OF THE INVENTION

The invention relates to a combined process for preparing diaryl carbonate and concentrating wastewater containing sodium chloride by osmotic distillation with simultaneous dilution of the sodium hydroxide solution obtained from the electrolysis for the diphenyl carbonate production process.

The preparation of diaryl carbonates (diphenyl carbonate) is usually carried out by means of a continuous process by preparation of phosgene and subsequent reaction of monophenols and phosgene in an inert solvent in the presence of alkali and a nitrogen catalyst in the interface.

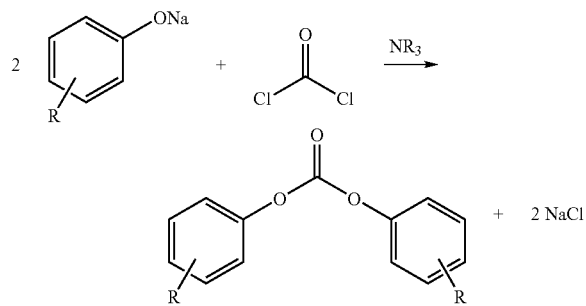

The preparation of diaryl carbonates, e.g. by the phase interface process, is described in principle in the literature, e.g. in Chemistry and Physics of Polycarbonates, Polymer Reviews, H. Schnell, Vol. 9, John Wiley and Sons, Inc. (1964), pp. 50/51.

U.S. Pat. No. 4,016,190 describes a process for preparing diaryl carbonates, which is operated at temperatures of >65° C. The pH is firstly set to a low value (pH 8 to 9) and subsequently a high value (10 to 11) in this process.

Optimization of the process by improving mixing and adherence to a narrow temperature and pH profile and isolation of the product are described in EP1219589 A1, EP1216981 A2, EP1216982 A2 and EP784048 A1.

However, a high residual phenol value in the wastewater from these known processes, which can pollute the environment and pose increased wastewater problems for the water treatment works, makes complicated purification operations necessary. Thus, WO 03/070639 A1 describes removal of the organic impurities in the wastewater by extraction with methylene chloride.

The solution containing sodium chloride is usually freed of solvents and organic residues and then disposed of.

According to EP 1200359 B1 (WO2000078682 A1) or U.S. Pat. No. 6,340,736, the wastewater containing sodium chloride can be purified by ozonolysis and then used in the electrolysis of sodium chloride. A disadvantage of this process is the very costly ozonolysis.

According to EP 541114 A2, a wastewater stream containing sodium chloride is evaporated to remove the water completely and the salt which remains together with the organic impurities is subjected to a thermal treatment, as a result of which the organic constituents are decomposed. Particular preference is given here to the use of infrared radiation. A disadvantage of the process is that the water has to be evaporated completely, so that the process cannot be carried out economically.

According to WO 03/70639 A1, the wastewater from DPC production is purified by extraction and then fed to the electrolysis of sodium chloride. However, only a maximum of 26% of the sodium chloride from the wastewater from DPC production can be recycled in the NaCl electrolysis since in the case of larger amounts of NaCl-containing wastewater the water introduced with the NaCl-containing wastewater into the electrolysis would upset the water balance of the sodium chloride electrolysis.

The solutions containing sodium chloride which are obtained in DPC production typically have a sodium chloride content of from 13 to 17% by weight. The entire sodium chloride present in the solutions can therefore never be recycled to the NaCl electrolysis to form chlorine and sodium hydroxide. At a sodium chloride concentration of 17% by weight in the standard sodium chloride electrolysis using a commercial ion-exchange membrane, which displays a water transport of 3.5 mol of water per mol of sodium, only about 23% of the sodium chloride from the solutions containing sodium chloride can be used. Increasing the concentration to about 25% by weight of a saturated sodium chloride solution would allow 38% of the sodium chloride present in the solution containing sodium chloride to be recycled. Recycling of all the solution containing sodium chloride is not known at present.

On the other hand, concentration processes by means of which water is withdrawn from the wastewater containing alkali metal chloride are known.

According to WO 01/38419, the solution containing sodium chloride can be evaporated by means of thermal processes so that a highly concentrated sodium chloride solution can be fed to the electrolysis cell. However, the evaporation is energy-intensive and costly.

It is also possible to use, for example, reverse osmosis or particularly preferably membrane distillation or membrane contactors (see MELIN; RAUTENBACH, Membran-verfahren; SPRINGER, BERLIN, 2003). A disadvantage here is the high energy consumption for overcoming the high osmotic pressures, as a result of which the process is no longer economical.

The abovementioned integrated processes all have the disadvantage that, in combination with a preparation of diaryl carbonate, it is possible to feed concentrated NaCl solutions (10-20% by weight) to the electrolysis only to a limited extent, so that NaCl can be reused only partially or increasing the concentration is energy-intensive and costly.

In view of the abovementioned prior art, it is an object of the invention to provide a process for preparing diaryl carbonate which gives products in high purity and good yield and enables a reduction in environmental pollution and wastewater problems in the water treatment works to be achieved by maximized recirculation of process wastewater solutions originating from diaryl carbonate production.

Furthermore, the conversion of sodium chloride into chlorine and sodium hydroxide and, if appropriate, hydrogen by electrolysis should be effected with minimal energy consumption and therefore in a resource-conserving manner in the recycling process.

The object is achieved by utilizing wastewater phases containing sodium chloride in the process by means of a preceding concentration increase of the NaCl solution from the preparation of diaryl carbonate for the electrolysis by means of an osmotic membrane distillation.

It has been found that the wastewater solutions containing sodium chloride which are obtained in the continuous preparation of diaryl carbonates by reaction of monophenols and phosgene in an inert solvent in the presence of alkali and a nitrogen catalyst in the phase interface can be concentrated directly, without complicated purification, in an osmotic membrane distillation after adjustment of the pH to a value of less than or equal to 8 and simple treatment with activated carbon and can be fed to an electrochemical oxidation of the sodium chloride present to chlorine, sodium hydroxide and, if appropriate, hydrogen, with the chlorine being able to be recycled at least partly for the preparation of phosgene.

BRIEF DESCRIPTION OF THE DRAWING

FIG. 1 depicts a process according to the invention for preparing DPC by phase interface phosgenation of Na phenoxide and utilization of the wastewater phases containing sodium chloride for electrolysis by increase of concentration using osmotic membrane distillation with simultaneous dilution of the sodium hydroxide solution obtained from the electrolysis for the diphenyl carbonate production process

EMBODIMENTS OF THE INVENTION

An embodiment of the present invention is a process for preparing diaryl carbonate comprising:
a) preparing phosgene by reacting chlorine with carbon monoxide;
b) reacting the phosgene formed in step a) with at least one monophenol in the presence of an aqueous alkali metal-containing base and, optionally, a nitrogen catalyst, to form a diaryl carbonate and a reaction wastewater solution comprising alkali metal chloride;
c) separating and working-up the diaryl carbonate formed in step b);
e) increasing concentration of at least part of said reaction wastewater solution comprising alkali metal chloride remaining after step c) by osmotic membrane distillation;
f) electrochemically oxidizing at least part of said reaction wastewater solution comprising alkali metal chloride from e) to form chlorine, alkali metal hydroxide, and, optionally, hydrogen.

Another embodiment of the present invention is the above process, wherein said aqueous alkali metal-containing base is a sodium-containing base and said alkali metal chloride is sodium chloride.

Another embodiment of the present invention is the above process, wherein, in a step d), solvent residues and, optionally, catalyst residues remaining after step c) are separated from said reaction wastewater solution comprising alkali metal chloride and subsequently the solution is fed to the osmotic membrane distillation in step e).

Another embodiment of the present invention is the above process, wherein said separating is performed by extraction or stripping of the solution by means of steam and/or treatment with an adsorbent.

Another embodiment of the present invention is the above process, wherein said adsorbent is activated carbon.

Another embodiment of the present invention is the above process, wherein concentration of said reaction wastewater solution comprising alkali metal chloride from d) is increased by means of osmotic distillation in step e) using sodium hydroxide solution as water acceptor.

Another embodiment of the present invention is the above process, wherein the osmotic membrane distillation in step e) is carried out at a temperature in the range of from 20 to 50° C.

Another embodiment of the present invention is the above process, wherein the osmotic membrane distillation in step e) is carried out at an absolute pressure in the range of from 1.1 to 1.2 bar.

Another embodiment of the present invention is the above process, wherein the osmotic membrane distillation in step e) is carried out at a differential pressure in the range of from 30 to 100 bar.

Another embodiment of the present invention is the above process, wherein the osmotic membrane distillation of at least part of said reaction wastewater solution comprising alkali metal chloride from d) is carried out using an Accurel PP membrane.

Another embodiment of the present invention is the above process, wherein the electrochemical oxidation of at least part of said reaction wastewater solution comprising alkali metal chloride from e) to chlorine and sodium hydroxide is carried out using gas diffusion electrodes as cathode.

Another embodiment of the present invention is the above process, wherein at least part of the purified reaction wastewater solution comprising alkali metal chloride from e) is introduced into the brine circuit of a membrane electrolysis for the preparation of chlorine and sodium hydroxide.

Another embodiment of the present invention is the above process, wherein additional alkali metal chloride is added to said reaction wastewater solution comprising alkali metal chloride to increase the alkali metal chloride concentration in the electrolysis f).

Another embodiment of the present invention is the above process, wherein said reaction wastewater solution comprising alkali metal chloride is brought to a pH of less than 8 in the isolation in step c) or the purification in step d).

Another embodiment of the present invention is the above process, wherein the pH of said reaction wastewater solution comprising alkali metal chloride is adjusted by use of hydrochloric acid or hydrogen chloride in the isolation in step c) or the purification in step d).

Another embodiment of the present invention is the above process, wherein the alkali metal chloride concentration of said reaction wastewater solution comprising alkali metal chloride fed to the electrolysis in step f) is in the range of from 100 to 280 g/l and/or the concentration of the alkali metal chloride solution obtained from the electrolysis in step f) is in the range of from 13 to 50% by weight.

Another embodiment of the present invention is the above process, wherein the alkali metal chloride concentration of said reaction wastewater solution comprising alkali metal chloride fed to the electrolysis in step f) is in the range of from 110 to 220 g/l and/or the concentration of the alkali metal chloride solution obtained from the electrolysis in step f) is in the range of from 14 to 32% by weight Another embodiment of the present invention is the above process, wherein said at least one monophenol in step b) is of formula (I)

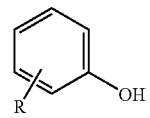

(I)

wherein R is hydrogen, halogen, or a branched or unbranched $C_1$-$C_9$-alkyl radical or alkoxycarbonyl radical.

Another embodiment of the present invention is the above process, wherein said at least one monophenol in step b) is selected from the group consisting of phenol, alkylphenols, and halophenols.

Another embodiment of the present invention is the above process, wherein said alkylphenols are selected from the group consisting of cresols, p-tert-butylphenol, p-cumylphenol, p-n-octylphenol, p-isooctylphenol, p-n-nonylphenol, and p-isononylphenol, and said halophenols are selected from the group consisting of p-chlorophenol, 2,4-dichlorophenol, p-bromophenol, and 2,4,6-tribromophenol.

Another embodiment of the present invention is the above process, wherein said at least one monophenol in step b) is phenol.

DESCRIPTION OF THE INVENTION

The invention therefore provides a process for preparing diaryl carbonate and utilizing the wastewater phases. In particular, the process comprises increasing concentration of the wastewater phases containing sodium chloride from the diphenyl carbonate production process (DPC process) for processing in a subsequent alkali metal chloride electrolysis by osmotic membrane distillation. At the same time, a sodium hydroxide solution formed in the electrolysis can be diluted so that it can subsequently be used directly as starting material in the DPC process.

Process for preparing diaryl carbonate, which comprises the following steps:
a) preparation of phosgene by reaction of chlorine with carbon monoxide,
b) reaction of the phosgene formed in step a) with at least one monophenol in the presence of an aqueous alkali metal-containing base, in particular a sodium-containing base, optionally a nitrogen catalyst and optionally an organic solvent to form a diaryl carbonate and a reaction wastewater solution containing alkali metal chloride, in particular sodium chloride,
c) separation and work-up of the diaryl carbonate formed in step b),
d) optionally separation of the solvent residues and optionally catalyst residues from the solution containing alkali metal chloride which remain after step c), in particular by extraction or stripping of the solution by means of steam and/or treatment with adsorbents, in particular activated carbon,
e) osmotic membrane distillation of at least part of the solution containing alkali metal chloride which remains after step c) or d),
f) electrochemical oxidation of at least part of the solution containing alkali metal chloride from e) to form chlorine, alkali metal hydroxide and if appropriate hydrogen.

In a particularly preferred embodiment, the process is characterized in that the solution is brought to a pH of less than or equal to 8, preferably from 6 to 8, in step c) or d) before treatment with adsorbents.

In a further particular embodiment, at least part of the chlorine produced in step f) is recycled to the preparation of phosgene of step a).

In a further preferred embodiment, at least part of the alkali metal hydroxide prepared in step f) is used as water acceptor in the osmotic membrane distillation of step e).

In a further particularly preferred embodiment, at least part of the dilute alkali metal hydroxide solution obtained is used for to the preparation of diaryl carbonate in step b).

The solution containing alkali metal chloride (reaction wastewater) obtained after the separation in step c) can be used either alone or in combination with the washing phases from the work-up (total process wastewater), preferably alone, in the osmotic membrane distillation after removal of solvent residues and optionally catalyst residues in step d).

Particularly suitable monophenols for use in the novel process are phenols of the formula (I)

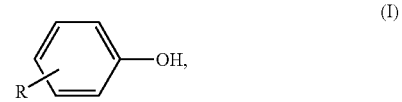

where
R is hydrogen, halogen or a branched or unbranched $C_1$-$C_9$-alkyl radical or alkoxycarbonyl radical.

Preference is given to phenol, alkylphenols such as cresols, p-tert-butylphenol, p-cumylphenol, p-n-octylphenol, p-isooctylphenol, p-n-nonylphenol and p-isononylphenol. Halophenols such as p-chlorophenol, 2,4-dichlorophenol, p-bromophenol and 2,4,6-tribromophenol or methyl salicylate. Particular preference is given to phenol.

The alkali used for forming the phenoxide in step b) can be, for example, an alkali solution containing hydroxides from the group consisting of Na hydroxide, K hydroxide, Li hydroxide, with preference being given to sodium hydroxide, and is preferably used as a from 10 to 55% strength by weight solution in the novel process. The alkali solution is particularly preferably used in an amount of from 1.0 to 1.1 molar equivalents based on phenol.

The reaction in step b) can be accelerated by nitrogen catalysts such as tertiary amines, N-alkylpiperidines or onium salts.

The amine catalyst used can be open-chain or cyclic, with preference being given to tributylamine, triethylamine and N-ethylpiperidine. The catalyst is preferably used as a from 1 to 55% strength by weight solution in the process of the invention.

The concentration of the catalyst is preferably from 0.0001 mol to 0.1 mol, based on the monophenol used.

For the present purposes, onium salts are compounds such as $NR_4X$, where R can be an alkyl and/or aryl radical and/or H and X is an anion.

In process step b), phosgene can be used as a liquid, gas or solution in an inert solvent.

Inert organic solvents which can preferably be used in step b) of the novel process are, for example, dichloromethane, toluene, the various dichloroethanes and chloropropane compounds, chlorobenzene and chlorotoluene. Preference is given to using dichloromethane.

The reaction in step b) is preferably carried out continuously and particularly preferably in plug flow without any great backmixing. This can thus occur, for example, in tube reactors. Mixing of the two phases (aqueous and organic phases) can be achieved by means of installed orifice plates, static mixers and/or, for example, pumps. The reaction in step b) can be carried out in one or two stages, particularly preferably in two stages.

If the process in step b) proceeds in two stages, the reaction is preferably started in the first stage of the process of the invention by combining the starting materials phosgene, the inert solvent, which preferably initially serves as solvent for the phosgene, and the monophenol, which has preferably been dissolved beforehand in the alkali metal hydroxide solution. The residence time in the first stage is typically in the range from 2 seconds to 300 seconds, particularly preferably in the range from 4 seconds to 200 seconds. The pH in the first stage is preferably set by means of the ratio of alkali metal hydroxide solution/monophenol/phosgene so that the pH is in the range from 11.0 to 12.0, preferably from 11.2 to 11.8, particularly preferably from 11.4 to 11.6. The reaction temperature in the first stage is preferably kept <40° C., particularly preferably <35° C., by cooling.

In a second stage of the process of the invention, the reaction to form diaryl carbonate is then preferably completed. The residence time in the preferred process is from 1 minute to 2 hours, preferably from 2 minutes to 1 hour, very particularly preferably from 3 minutes to 30 minutes. In the second stage of the preferred process, the pH is constantly monitored (preferably measured on-line by methods known in principle in the continuous process) and the pH is appropriately adjusted by addition of the alkali metal hydroxide. The amount of alkali metal hydroxide introduced is, in particular, set so that the pH of the reaction mixture in the second process stage is in the range from 7.5 to 10.5, preferably from 8 to 9.5, very particularly preferably from 8.2 to 9.3. The reaction temperature in the second stage is preferably kept <50° C., particularly preferably <40° C., very particularly preferably <35° C., by cooling.

However, the parameters or details mentioned in general terms or in preferred ranges in the present application can also be combined in any way with one another, i.e. between the respective ranges and preferred ranges.

In the preferred process, the molar ratio of phosgene to monophenol in step b) is from 1:2 to 1:2.2. The solvent is added in such an amount that the diaryl carbonate is present in a from 5 to 60% strength solution, preferably from 20 to 45% strength solution, after the reaction.

After the reaction b), the organic phase containing the diaryl carbonate is preferably washed with an aqueous liquid in step c) and after each washing operation is separated as completely as possible from the aqueous phase. Washing liquids used are aqueous liquids for separating off the catalyst, e.g, a dilute mineral acid such as HCl or $H_3PO_4$, preferably HCl, and deionized water for further purification. The diaryl carbonate solution is usually turbid after washing and removal of the washing liquid. The concentration of HCl or $H_3PO_4$ in the washing liquid can be, for example, from 0.5 to 1.0% by weight. The organic phase is, by way of example and preferably, washed twice.

As phase separation apparatuses for separating the washing liquid from the organic phase, it is in principle possible to use separation vessels, phase separators, centrifuges or coalescers known to those skilled in the art or combinations of these apparatuses.

High purities of the diaryl carbonate of >99.85%, disregarding the solvent still to be separated off, can be obtained by the process of the invention.

In a preferred embodiment, the diaryl carbonate is, after the synthesis of the diaryl carbonate, separated off in the form of its solution in the organic solvent used in the synthesis, for example methylene chloride.

To obtain the high-purity diaryl carbonate, the solvent is subsequently evaporated. The evaporation can be carried out in a plurality of evaporator stages. For example, it is carried out by means of one or more distillation columns connected in series in which the solvent is separated off from the diaryl carbonate.

The purification step c) can be carried out in one or more stages. The stages can, for example, be carried out continuously so that the temperature at the bottom in the distillation is from 150° C. to 310° C., preferably from 160 to 230° C. The pressure employed for carrying out this distillation is, in particular, from 1 to 1000 mbar, preferably from 5 to 100 mbar.

The diaryl carbonates which have been purified in this way have a particularly high purity (GC>99.95%) and extremely good transesterification behaviour, so that a polycarbonate of excellent quality can subsequently be produced therefrom.

The use of the diaryl carbonates for preparing aromatic oligocarbonates/polycarbonates by the melt transesterification process is known in the literature and described, for example, in Encyclopedia of Polymer Science, Vol. 10 (1969), Chemistry and Physics of Polycarbonates, Polymer Reviews, H. Schnell, Vol. 9, John Wiley and Sons, Inc. (1964) or U.S. Pat. No. 5,340,905.

The aqueous solution which remains in step c) is preferably freed of volatile organic impurities, e.g. residues of the organic solvent used in the synthesis and possibly remaining catalyst, by, for example, distillation or steam stripping. Wastewater having a content of dissolved sodium chloride (10-20% by weight) and dissolved sodium carbonates (0.3-1.5% by weight) then remains. The carbonates are formed, for example, by hydrolysis of phosgene as secondary reaction in the preparation of diaryl carbonate. The wastewater is additionally polluted with organic compounds, e.g. phenols (e.g. unsubstituted phenol, alkylphenols).

In a particularly preferred embodiment, the prepurified wastewater is treated with adsorbents, preferably with activated carbon.

According to a preferred process, the reduction in the pH in process step c) or d) is carried out using hydrochloric acid or gaseous hydrogen chloride.

In a preferred process variant, water is withdrawn from the wastewater containing alkali metal chloride by means of a concentration process.

Concentration of NaCl solutions by osmotic distillation saves energy, particularly when the NaOH solution originating from the NaCl electrolysis is used as water acceptor. This is advantageous particularly when a dilute sodium hydroxide solution is used in DPC production, in which case the water for dilution of the sodium hydroxide can additionally be saved.

Particular preference is therefore given to a process which is characterized in that the concentration of the solution containing alkali metal chloride from d) is increased by means of osmotic distillation using sodium hydroxide solution as water acceptor (step e) prior to the electrolysis f).

Combining operation of the electrolysis cells according to the invention and concentration increase processes theoretically enables up to 100% of the sodium chloride to be recovered from the wastewater.

The osmotic distillation is effected by molecular and possibly Knudsen diffusion of water vapour through a membrane. The diffusion rate is dependent on the difference between the water vapour pressures on the two sides of the membrane and also its porosity, thickness and extent to which it is rolled up.

To make efficient concentration increase possible, a concentrated solution of an alkali metal hydroxide, preferably sodium or potassium hydroxide, particularly preferably sodium hydroxide, should be used as water acceptor.

For the purposes of the process of the invention, a chemically stable material such as polypropylene should be used as membrane material, The membranes used should preferably be capillary membranes having a capillary length of 30-6000 μm and a diameter of from 0.01 to 0.7 μm.

Particularly suitable membranes are lipophilic membranes such as Accurel PP 50/200, Accurel PP 50/280, Accurel PP 150/330, Accurel PP Q3/2 or Accurel S 6/2 from Membrana.

The process is preferably operated so that the osmotic distillation is carried out at a temperature of from 10 to 100° C., preferably from 20 to 50° C. The temperature of the sodium hydroxide solution used can be higher than that of the NaCl-containing wastewater.

The osmotic distillation is carried out at an absolute pressure of from 1 to 1.4 bar, preferably at a pressure of from 1.1 to 1.2 bar.

The pressure ratios between alkali metal chloride solution and alkali metal hydroxide solution are, in particular, selected so that the osmotic pressure of the alkali metal chloride solution is higher than the pressure of the alkali metal hydroxide solution.

The differential pressure between alkali metal chloride solution and alkali metal hydroxide solution should, in a particularly preferred process, be from 20 to 150 bar, preferably from 30 to 100 bar.

The process of alkali metal chloride electrolysis is described in more detail below. The following description should be considered to be illustrative in respect of the electrolysis of sodium chloride, since any alkali metal chloride (in particular LiCl, NaCl, KCl) can in principle be used in the process, as indicated above; however, the use of sodium chloride and sodium hydroxide in the stages carried out is the preferred embodiment of the process.

Membrane electrolysis processes are usually used, for example, for the electrolysis of solutions containing sodium chloride (on this subject, see Peter Schmittinger, CHLORINE, Wiley-VCH Verlag, 2000). Here, an electrolysis cell which is divided in two and comprises an anode space with an anode and a cathode space with a cathode is used, Anode space and cathode space are separated by an ion-exchange membrane. A solution containing sodium chloride and having a sodium chloride concentration of usually more than 300 g/l is introduced into the anode space. At the anode, the chloride ion is oxidized to chlorine which is discharged from the cell with the depleted sodium chloride solution (about 200 g/l). The sodium ions migrate under the action of the electric field through the ion-exchange membrane into the cathode space. During this migration, each mol of sodium carries with it from 3.5 to 4.5 mol of water, depending on the membrane. This leads to the anolyte becoming depleted in water. In contrast to the anolyte, water is consumed on the cathode side by the electrolysis of water to form hydroxide ions and hydrogen. The water carried with the sodium ions into the catholyte is sufficient to keep the sodium hydroxide concentration in the output at 31-32% by weight, at an inlet concentration of 30% and a current density of 4 kA/m$^2$. In the cathode space, water is electrochemically reduced to form hydroxide ions and hydrogen.

As an alternative, a gas diffusion electrode at which oxygen is reacted with electrons to form hydroxide ions and no hydrogen is formed can be used as cathode. The hydroxide ions together with the sodium ions which have migrated into the cathode space via the ion-exchange membrane form sodium hydroxide. A sodium hydroxide solution having a concentration of 30% by weight is usually fed into the cathode chamber and a sodium hydroxide solution having a concentration of 31-32% by weight is discharged. The aim is to achieve a very high concentration of sodium hydroxide since the sodium hydroxide is usually stored or transported as a 50% strength solution. However, commercial membranes are at present not resistant to an alkali solution having a concentration greater than 32% by weight, so that the sodium hydroxide solution has to be concentrated by thermal evaporation.

In the case of the electrolysis of sodium chloride, additional water is introduced into the anolyte via this solution containing sodium chloride, but water is only discharged into the catholyte via the membrane. If more water is introduced via the solution containing sodium chloride than can be transported to the catholyte, the anolyte becomes depleted in sodium chloride and the electrolysis cannot be operated continuously. In the case of very low sodium chloride concentrations, the secondary reaction of oxygen formation would occur.

To feed maximal amounts of solutions containing sodium chloride economically into the electrolysis of sodium chloride, it can be useful to increase the water transport through the membrane. This can be effected by choice of suitable membranes, as described in U.S. Pat. No. 4,025,405. The effect of increased water transport is that the otherwise customary addition of water to maintain the alkali concentration can be dispensed with.

According to U.S. Pat. No. 3,773,634, at increased water transport through the membrane, the electrolysis can be operated when an alkali concentration of from 31 to 43% by weight and a sodium chloride concentration of from 120 to 250 g/l are used.

In the preferred process, the isolation d) of the reaction wastewater containing sodium chloride after phase separation and the removal of the solvent and possibly catalyst used is effected by extraction or stripping with steam and, after adjustment of the pH, by treatment with activated carbon.

The wastewater containing alkali metal chloride can then be fed directly to the osmotic distillation e).

Compared to the prior art (WO 03/70639), in which a maximum of 26% of the sodium chloride present in the wastewater from DPC production can be used in the electrolysis of NaCl, more than 26% of the sodium chloride can be recovered from the wastewater in the process of the invention.

The novel process can also be carried out using an alkali metal chloride electrolysis in which no hydrogen is generated at the cathode but the cathode is instead replaced by a gas diffusion electrode at which oxygen is reduced to hydroxide ions.

When, for example, no hydrogen is required for chemical reactions at an integrated production site, the formation of hydrogen as necessary coproduct can be dispensed with. An advantage is an energy saving in the electrolysis, attributable to the lower electrolysis voltage when using a gas diffusion electrode.

The solution containing sodium chloride coming from DPC production usually has a sodium chloride content of up to 18% by weight insofar as it is the reaction wastewater. If the reaction wastewater is contaminated with the washing water, the NaCl concentration is, for example, about 13% by weight. If the electrolysis provides the chlorine and the sodium hydroxide exclusively for DPC production, only a small part of the wastewater containing sodium chloride can be used in the electrolysis. Thus, in the case of conventional ion-exchange membranes and the standard operating parameters for the electrolysis of sodium chloride, only a maximum of 26% of the sodium chloride of a 17% strength by weight DPC wastewater containing sodium chloride can be used. The standard operating parameters of the NaCl electrolysis are a brine concentration in the outflow of from 200 to 240 g/l and an NaOH concentration of 31-32% by weight. Total recycling of the sodium chloride obtained has therefore not been possible hitherto. Concentration by thermal evaporation of the water is at present not economical since the sodium chloride is available as very inexpensive product.

Significantly more than 26% of the sodium chloride in wastewater obtained having a concentration of 17% by weight can be recycled by means of the process of the invention as long as the sodium chloride electrolysis exclusively provides the chlorine and the sodium hydroxide for DPC production. At integrated chemical sites, sodium chloride electrolyses are usually operated with a plurality of chlorine consumers, so that a solution containing sodium chloride is not available for recycling from all consumers. The proportion of reusable sodium chloride from the wastewater increases when the sodium chloride electrolysis does not have to provide the sodium hydroxide and the chlorine exclusively for diaryl carbonate production.

In a further preferred variant of the novel process, the wastewater from diaryl carbonate production is concentrated by means of solid alkali metal chloride and fed to the alkali metal chloride electrolysis. In this way, more than 50% of the alkali metal chloride in the DPC wastewater can be reused.

However, a prerequisite for this is that the chlorine and the alkali metal hydroxide are not used exclusively for diaryl carbonate production.

In the electrolysis f), particular preference is given to using or feeding in a wastewater containing alkali metal chloride which has a pH of less than 7. The adjustment of the pH is preferably carried out using hydrochloric acid but can also be carried out using gaseous hydrogen chloride.

In a further preferred process, the NaCl electrolysis is operated so that the NaCl solution leaving the cell has an NaCl concentration of less than 200 g/l. In parallel thereto, the alkali concentration flowing out from the cell can be less than 30% by weight.

The water transport through the ion-exchange membrane depends not only on the operating parameters but also on the type of membrane used. In the process of the invention, preference is given to using ion-exchange membranes which, under the conditions of sodium chloride and alkali concentration according to the invention, allow water transport through the membrane of more than 4.5 mol of water per mol of sodium.

The current density is calculated on the basis of the membrane area and is, in particular, from 2 to 6 kA/m$^2$. Particular preference is given to using anodes having a relatively large surface area. For the purposes of the present invention, anodes having a relatively large surface area are ones in which the physical surface area is significantly higher than the projected surface area. Anodes having a relatively large surface area are, for example, foam- or felt-like electrodes. In this way, a very large electrode surface area is offered on the anode side and the local current density is greatly reduced. The surface area of the anode is preferably selected so that the local current density based on the physical surface area of the electrode is less than 3 kA/m$^2$. The greater the surface area and the lower the local current density, the smaller can be the sodium chloride concentration in the brine be and the higher the proportion of sodium chloride from the wastewater which can be recycled.

The pH of the wastewater containing alkali metal chloride should preferably be less than 7, particularly preferably from 0.5 to 6, prior to the electrolysis f).

The alkali metal chloride electrolysis should be operated so that the alkali metal chloride concentration of the alkali metal chloride solution leaving the cell is from 100 to 280 g/l of sodium chloride and/or the concentration of the alkali solution leaving the cell is from 13 to 33% by weight.

Particular preference is given to concentrations which make operation of the cell at relatively low voltages possible. To achieve this, the concentration of the alkali metal chloride solution leaving the cell should preferably be from 110 to 220 g/l of alkali metal chloride and/or the concentration of the alkali solution leaving the cell should be from 20 to 30% by weight.

The ion-exchange membranes used in the electrolysis should preferably have a water transport per mol of sodium of more than 4.0 mol of $H_2O$/mol of sodium, particularly preferably from 4.5 to 6.5 mol of $H_2O$/mol of sodium.

The process is preferably operated so that the electrolysis f) is carried out at a temperature of from 70 to 100° C., preferably from 80 to 95° C.

The electrolysis is carried out at an absolute pressure of from 1 to 1.4 bar, preferably at a pressure of from 1.1 to 1.2 bar.

The pressure ratios between anode space and cathode space are, in particular, selected so that the pressure in the cathode space is higher than the pressure in the anode space.

The differential pressure between cathode space and anode space should, in a particularly preferred process, be from 20 to 150 mbar, preferably from 30 to 100 mbar.

At relatively low alkali metal chloride concentrations, it is also possible to use specific anode coatings. In particular, the coating of the anode can contain ruthenium oxide together with further noble metal components of transition groups 7 and 8 of the Periodic Table of the Elements. For example, the anode coating can be doped with palladium compounds. Coatings based on diamonds can likewise be used.

FIG. 1: Schematic depiction of a process according to the invention for preparing DPC by phase interface phosgenation of Na phenoxide and utilization of the wastewater phases containing sodium chloride for electrolysis by increasing concentration using osmotic membrane distillation with simultaneous dilution of the sodium hydroxide solution obtained from the electrolysis for the diphenyl carbonate production process.

The following examples illustrate the present invention without restricting it.

All the references described above are incorporated by reference in their entireties for all useful purposes.

While there are shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

The examples are intended to illustrate the process of the invention with the aid of the concentration of the wastewater phases containing sodium chloride which are obtained in the preparation of diphenyl carbonate and simultaneous dilution of the sodium hydroxide solution obtained from the electrolysis for the diphenyl carbonate production process (DPC process) by osmotic membrane distillation and electrolysis of the solutions containing sodium chloride which are obtained.

Example 1 a) Preparation and Work-Up of Diphenyl Carbonate

In a vertical, cooled tube reactor, a mixture of 145.2 kg/h of 14.5% strength sodium hydroxide solution, produced by diluting 65.8 kg/h of a 32.0% strength sodium hydroxide solution with 79.4 kg/h of deionized water (DI water), and 48.3 kg/h of phenol was continuously combined with a solution of 86.2 kg/h of methylene chloride and 27.5 kg/h of phosgene (8 mol % excess based on phenol). This reaction mixture was cooled to a temperature of 33° C. and after an average residence time of 15 seconds, a pH of 11.5 was measured. In the second stage of the process, 5.4 kg/h of 50.0% strength NaOH were then metered into this reaction mixture so that the pH of the second reaction stage after a further residence time of 5 minutes is 8.5. In the second stage of the process, the reaction mixture was mixed continually by passage through a tube provided with constrictions. The reaction temperature was, after renewed addition of the NaOH, set to 30° C. by cooling. After the organic phase had been separated off from the aqueous phase (reaction wastewater), the DPC solution was washed with 0.6% strength hydrochloric acid and water. Removal of the solvent gave 99.9% strength diphenyl carbonate. The reaction wastewater was not combined with the washing phases and was freed of solvent residues and catalysts by stripping with steam. After neutralization (pH 7) with hydrochloric acid and treatment with activated carbon, the reaction wastewater contained 17.0% of NaCl and <2 ppm of phenol.

The wastewater could be fed without further purification to the osmotic distillation.

b) Increasing Concentration of the Sodium Chloride Solution by Osmotic Membrane Distillation The reaction wastewater from a) was fed to the osmotic membrane distillation.

The osmotic distillation was carried out in a module having a membrane area of 1.1 m². An Accurel PP 150/330 membrane from Membrana was used. At room temperature, 1.7 l of the reaction wastewater solution containing 17.0% of sodium chloride from a) were pumped into the module while at the same time 0.6 l of 32.0% strength sodium hydroxide solution were fed in cocurrent as water acceptor phase. The concentration of the NaCl-containing solution leaving the cell was 21.9% by weight of NaCl, while the NaOH solution taken off displayed a concentration of 16.4% by weight.

c) Electrochemical Oxidation of the Sodium Chloride Solution from the Osmotic Distillation The electrolysis was carried out in a laboratory electrolysis cell having an anode area of 0.01 m². The current density was 4 kA/m², the temperature at the output from the cathode side was 88° C. and the temperature at the output from the anode side was 89° C. An electrolysis cell having standard anode and cathode coatings from DENORA, Germany, was used. A Nafion 982 WX ion-exchange membrane from DuPont was used. The electrolysis voltage was 3.02 V. A solution containing sodium chloride was pumped at a mass flow rate of 0.8 kg/h through the anode chamber. The concentration of the solution fed to the anode chamber was 25.0% by weight of NaCl. An 18.8% strength by weight NaCl solution could be taken off from the anode chamber. 0.152 kg/h of a 21.9% strength by weight reaction wastewater from the preparation of diphenyl carbonate under b) and 0.054 kg/h of solid sodium chloride were added to the NaCl solution taken off from the anode chamber. The solution was subsequently fed back into the anode chamber. The water transport through the membrane was 3.8 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 32.7% of NaOH , 0.182 kg/h of the 32.7% strength alkali was taken off from the volume stream, and the remainder was made up with 0.0539 kg/h of water and recirculated to the cathode element.

37.8% of the sodium chloride reacted came from the reaction wastewater from DPC production.

d) Recycling of the Dilute Sodium Hydroxide Solution from the Osmotic Distillation for the DPC Production The dilute sodium hydroxide solution from b) was fed to the preparation of diphenyl carbonate. A mixture of 145.2 kg/h of 14.5% strength sodium hydroxide solution, produced by diluting 128.4 kg/h of the 16.4% strength sodium hydroxide solution from b) with 16.8 kg/h of deionized water (DI water), and 48.3 kg/h of phenol was combined with a solution of 86.2 kg/h of methylene chloride and 27.5 kg/h of phosgene (8 mol % excess based on phenol) and processed as described in 1a).

The use of the 16.4% strength sodium hydroxide solution instead of the usual 32.0% strength sodium hydroxide solution enables 62.7 kg/h (78.9%) of DI water to be saved.

Example 2 a) Preparation and Work-Up of Diphenyl Carbonate

The procedure of Example 1a) was repeated, but the reaction wastewater was combined with the washing phases to give a total process wastewater and the latter was freed of solvent residues and catalyst by stripping with steam. After neutralization with hydrochloric acid and treatment with activated carbon, the total process wastewater contained 13.0% of NaCl and <2 ppm of phenol.

The wastewater could be fed without further purification to the osmotic membrane distillation.

b) Increasing Concentration of the Sodium Chloride Solution by Osmotic Membrane Distillation The osmotic distillation was carried out at room temperature in a module having a 1.1 m² membrane module equipped with an Accurel PP 150/330 membrane from Membrana. The process wastewater containing 13.0% of sodium chloride from a) was pumped at a flow rate of 21.0 l/h into the laboratory cell, while 12.1 l/h of 32.0% strength sodium hydroxide solution was metered in cocurrent as water acceptor. The concentration of the process wastewater solution leaving the cell was 24.1% by weight of NaCl, while the NaOH solution taken off had been depleted to 16.1% by weight.

The concentrated total process wastewater solution leaving the cell can be fed without further purification to the electrolysis.

c) Electrochemical Oxidation of the Sodium Chloride Solution from the Osmotic Distillation The electrolysis was carried out in a laboratory electrolysis cell having an anode area of 0.01 m². The current density was 4 kA/m², the temperature at the output from the cathode side was 88° C. and the temperature at the output from the anode side was 89° C. An electrolysis cell having standard anode and cathode coatings from DENORA, Germany, was used. A Nafion 982 WX ion-exchange membrane from DuPont was used, The electrolysis voltage was 3.02 V. A solution containing sodium chloride was pumped at a mass flow rate of 0.8 kg/h through the anode chamber. The concentration of the solution fed to the anode chamber was 25.0% by weight of NaCl. An 18.8% strength by weight NaCl solution could be taken off from the anode chamber, 0.157 kg/h of 24.1% strength by weight enriched total process wastewater from the osmotic distillation under b) and 0.505 kg/h of solid sodium chloride were added to the NaCl solution taken off from the anode chamber. The solution was subsequently fed back into the anode chamber. The water transport through the membrane was 3.8 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 32.7% of NaOH. 0.182 kg/h of the 32.7% strength alkali was taken off from the volume stream, and the remainder was made up with 0.0539 kg/h of water and recirculated to the cathode element. 42.8% of the sodium chloride reacted came from the DPC total process wastewater.

d) Recycling of the Dilute Sodium Hydroxide Solution from the Osmotic Distillation for the DPC Production The dilute sodium hydroxide solution from b) was fed to the preparation of diphenyl carbonate. A mixture of 145.2 kg/h of 14.5% strength sodium hydroxide solution, produced by diluting 130.8 kg/h of the 16.1% strength sodium hydroxide solution from b) with 14.4 kg/h of deionized water (DI water), and 48.3 kg/h of phenol was combined with a solution of 86.2 kg/h of methylene chloride and 27.5 kg/h of phosgene (8 mol % excess based on phenol) and processed as described in 1a).

The use of the 16.1% strength sodium hydroxide solution instead of the usual 32.0% strength sodium hydroxide solution enabled 65.0 kg/h (81.8%) of DI water to be saved.

Example 3 a) Preparation and Work-Up of Diphenyl Carbonate

The procedure of Example 2a) was repeated, with the reaction wastewater being combined with the washing phases to give a total process wastewater and the latter being freed of solvent residues and catalyst by stripping with steam. After neutralization with hydrochloric acid and treatment with activated carbon, the total process wastewater contained 13.0% of NaCl and <2 ppm of phenol.

The wastewater could be fed without further purification to the osmotic membrane distillation.

b) Increasing Concentration of the Sodium Chloride Solution by Osmotic Membrane Distillation The osmotic membrane distillation was carried out at room temperature in a laboratory cell having a 2 m$^2$ membrane module equipped with an Accurel PP 150/330 membrane from Membrana. The process wastewater containing 13.0% of sodium chloride from a) was pumped at a flow rate of 3.0 l/h into the laboratory cell, while 3.0 l/h of 31.4% strength sodium hydroxide solution was metered in cocurrent as water acceptor. The concentration of the process wastewater solution leaving the cell was 19.5% by weight of NaCl, while the NaOH solution taken off had been depleted to 20.0% by weight.

The concentrated process wastewater solution leaving the cell could be fed without further purification to the electrolysis.

c) Electrochemical Oxidation of the Sodium Chloride Solution from the Osmotic Distillation The electrolysis was carried out in a laboratory electrolysis cell having an anode area of 0.01 m$^2$. The current density was 4 kA/m$^2$, the temperature at the output from the cathode side was 88° C. and the temperature at the output from the anode side was 89° C. An electrolysis cell having standard anode and cathode coatings from DENORA, Germany, was used, A Nafion 982 WX ion-exchange membrane from DuPont was used. The electrolysis voltage was 3.02 V. A solution containing sodium chloride was pumped at a mass flow rate of 0.8 kg/h through the anode chamber. The concentration of the solution fed to the anode chamber was 25.0% by weight of NaCl. An 18.8% strength by weight NaCl solution could be taken off from the anode chamber, 0.147 kg/h of 19.5% strength by weight enriched total process wastewater from the osmotic membrane distillation under b) and 0.0594 kg/h of solid sodium chloride were added to the NaCl solution taken off from the anode chamber. The solution was subsequently fed back into the anode chamber. The water transport through the membrane was 3.8 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 32.7% of NaOH. 0.182 kg/h of the 32.7% strength alkali was taken off from the volume stream, and the remainder was made up with 0.0539 kg/h of water and recirculated to the cathode element.

32.7% of the sodium chloride reacted came from the DPC total process wastewater.

d) Recycling of the Dilute Sodium Hydroxide Solution from the Osmotic Distillation for the DPC Production The dilute sodium hydroxide solution from b) was fed to the preparation of diphenyl carbonate. A mixture of 145.2 kg/h of 14.5% strength sodium hydroxide solution, produced by diluting 105.0 kg/h of the 20.0% strength sodium hydroxide solution from b) with 40.0 kg/h of deionized water (DI water), and 48.3 kg/h of phenol was combined with a solution of 86.2 kg/h of methylene chloride and 27.5 kg/h of phosgene and processed as described in 1a).

The use of the 20.0% strength sodium hydroxide solution instead of the usual 32.0% strength sodium hydroxide solution enables 39.4 kg/h (49.6%) of DI water to be saved.

Comparative Example 4

Reworking of Example 1 from DE 102006041465 A1 a) Isolation of the Reaction Wastewater from DPC Production

The wastewater corresponded to the quality in Example 1a). The reaction wastewater was not combined with the washing phases and was freed of solvent residues and catalyst by stripping with steam. After neutralization with hydrochloric acid and treatment with activated carbon, the reaction wastewater contained 17.0% by weight of NaCl and less than 2 ppm of phenol.

The wastewater could be fed without further purification to the sodium chloride electrolysis cell.

b) Electrochemical Oxidation of the Reaction Wastewater from a)

The electrolysis was carried out in a laboratory electrolysis cell having an anode area of 0.01 m$^2$. The current density was 4 kA/m$^2$, the temperature at the output from the cathode side was 88° C. and the temperature at the output from the anode side was 89° C. An electrolysis cell having standard anode and cathode coatings from DENORA, Germany, was used. A Nafion 982 WX ion-exchange membrane from DuPont was used. The electrolysis voltage was 3.02 V. A solution containing sodium chloride was pumped at a mass flow rate of 0.81 g/h through the anode chamber. The concentration of the solution fed to the anode chamber was 25.0% by weight of NaCl. An 18.6% strength by weight NaCl solution could be taken off from the anode chamber. 0.133 kg/h of 17.0% strength by weight reaction wastewater from diphenyl carbonate production in Example 1a) and 0.0655 kg/h of solid sodium chloride were added to the NaCl solution taken off from the anode chamber. The solution was subsequently fed back into the anode chamber, The water transport through the membrane was 3.5 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 33.0% of NaOH. 0.180 kg/h of the 33.0% strength alkali was taken off from the volume stream, and the remainder was made up with 0.060 kg/h of water and recirculated to the cathode element.

Only 25.8% of the sodium chloride reacted came from the DPC reaction wastewater.

Comparative Example 5 a) Isolation of the Reaction Wastewater from DPC Production

The wastewater corresponded to the quality in Example 2a). The reaction wastewater was combined with the washing phases and was freed of solvent residues and catalyst by stripping with steam. After neutralization with hydrochloric acid and treatment with activated carbon, the total process wastewater contained 13.0% by weight of NaCl and less than 2 ppm of phenol.

The wastewater could be fed without further purification to the sodium chloride electrolysis cell.

b) Electrochemical Oxidation of the Total Process Wastewater

The electrolysis was carried out in a laboratory electrolysis cell having an anode area of 0.01 m$^2$. The current density was 4 kA/m$^2$, the temperature at the output from the cathode side was 88° C. and the temperature at the output from the anode side was 89° C. An electrolysis cell having standard anode and cathode coatings from DENORA, Germany, was used. A Nafion 982 WX ion-exchange membrane from DuPont was used. The electrolysis voltage was 3.02 V. A solution containing sodium chloride was pumped at a mass flow rate of 0.8 kg/h through the anode chamber. The concentration of the solution fed to the anode chamber was 25.0% by weight of NaCl. An 18.6% strength by weight NaCl solution could be taken off from the anode chamber. 0.127 kg/h of 13.0% strength by weight reaction wastewater from diphenyl carbonate production in Example 1a) and 0.0717 kg/h of solid sodium chloride were added to the NaCl solution taken off from the anode chamber. The solution was subsequently fed back into the anode chamber. The water transport through the membrane was 3.5 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 33.0% of NaOH. 0.180 kg/h of the 33.0% strength alkali was taken off from the volume stream, and the remainder was made up with 0.060 kg/h of water and recirculated to the cathode element.

Only 18.8% of the sodium chloride reacted came from the DPC total process wastewater.

Comparative Example 6

Reworking of Example 2 from DE 102006041465 A1 a) Isolation of the Reaction Wastewater from DPC Production

The wastewater corresponded to the quality in Example 1a).

b) Electrochemical Oxidation of the Reaction Wastewater Using Gas Diffusion Electrodes Since no hydrogen is required for the preparation of DPC, the formation of hydrogen in the electrolysis can be dispensed with. The electrolysis was therefore operated using gas diffusion electrodes. The current density was 4 kA/m$^2$, the temperature at the output from the cathode side was 88° C. and the temperature at the output from the anode side was 89° C. An electrolysis cell having standard anode coating from DENORA, Germany, was used. A Nafion 982 WX ion-exchange membrane from DuPont was used. The electrolysis voltage was 2.11 V. The sodium chloride concentration of the solution taken off from the anode chamber was 17.0% by weight of NaCl. 0.178 kg/h of 17.0% strength by weight reaction wastewater and 0.0579 kg/h of solid sodium chloride were added to the NaCl solution taken off from the anode chamber. The solution was subsequently fed back into the anode chamber. The water transport through the membrane was 4.9 mol of water per mol of sodium.

A sodium hydroxide solution was pumped at a mass flow rate of 0.653 kg/h through the cathode side. The concentration of the sodium hydroxide solution fed into the cathode side was 30.0% by weight of NaOH, and the sodium hydroxide solution taken off from the cathode side had a concentration of 31.5% by weight of NaOH. 0.189 kg/h of the 31.5% strength alkali was taken off from the volume stream, and the remainder was made up with 0.0312 kg/h of water and recirculated to the cathode element.

The proportion of sodium chloride reacted from the DPC reaction wastewater was 34.4%.

The examples show that a significantly higher degree of recycling of the sodium chloride in the wastewater solutions from the DPC production process to the electrolysis is achieved after increasing concentration by osmotic membrane distillation, with the water taken up by the alkali solution being able to be saved in the production of the alkali metal hydroxide solution in the DPC production step.

The invention claimed is:

1. A process for preparing diaryl carbonate comprising:
   a) preparing phosgene by reacting chlorine with carbon monoxide;
   b) reacting the phosgene formed in step a) with at least one monophenol in the presence of an aqueous alkali metal-containing base and, optionally, a nitrogen catalyst, to form a diaryl carbonate and a reaction wastewater solution comprising alkali metal chloride;
   c) separating and working-up the diaryl carbonate formed in step b);
   d) separating solvent residues and, optionally, catalyst residues from said reaction wastewater solution comprising alkali metal chloride remaining after step c) and subsequently feeding the solution to an osmotic membrane distillation in step e);
   e) increasing concentration of at least part of said reaction wastewater solution comprising alkali metal chloride from step d) by means of osmotic membrane distillation using an alkali metal hydroxide solution as water acceptor;
   f) electrochemically oxidizing at least part of said reaction wastewater solution comprising alkali metal chloride from e) to form chlorine, alkali metal hydroxide, and, optionally, hydrogen.

2. The process of claim 1, wherein said aqueous alkali metal-containing base is a sodium-containing base and said alkali metal chloride is sodium chloride.

3. The process of claim 1, wherein said separating in step d) is performed by extraction or stripping of the solution by means of steam and/or treatment with an adsorbent.

4. The process of claim 3, wherein said adsorbent is activated carbon.

5. The process of claim 1, wherein the osmotic membrane distillation in step e) is carried out at a temperature in the range of from 20 to 50° C.

6. The process of claim 1, wherein the osmotic membrane distillation in step e) is carried out at an absolute pressure in the range of from 1.1 to 1.2 bar.

7. The process of claim 1, wherein the osmotic membrane distillation in step e) is carried out at a differential pressure in the range of from 30 to 100 bar.

8. The process of claim 1, wherein the osmotic membrane distillation of at least part of said reaction wastewater solution comprising alkali metal chloride from d) is carried out using a lipophilic membrane.

9. The process of claim 1, wherein the electrochemical oxidation of at least part of said reaction wastewater solution comprising alkali metal chloride from e) to chlorine and alkali metal hydroxide is carried out using gas diffusion electrodes as cathode.

10. The process of claim 1, wherein at least part of the reaction wastewater solution comprising alkali metal chloride from e) is introduced into the brine circuit of a membrane electrolysis for the preparation of chlorine and alkali metal hydroxide.

11. The process of claim 1, wherein additional alkali metal chloride is added to said reaction wastewater solution comprising alkali metal chloride to increase the alkali metal chloride concentration in the electrolysis f).

12. The process of claim 1, wherein said reaction wastewater solution comprising alkali metal chloride is brought to a pH of less than 8 in the isolation in step c) or the distillation in step d).

13. The process of claim 12, wherein the pH of said reaction wastewater solution comprising alkali metal chloride is adjusted by use of hydrochloric acid or gaseous hydrogen chloride in the isolation in step c) or the distillation in step d).

14. The process of claim 1, wherein the alkali metal chloride concentration of said reaction wastewater solution comprising alkali metal chloride fed to the electrolysis in step f) is in the range of from 100 to 280 g/l and/or the concentration of the alkali hydroxide solution obtained from the electrolysis in step f) is in the range of from 13 to 50% by weight.

15. The process of claim 14, wherein the alkali metal chloride concentration of said reaction wastewater solution comprising alkali metal chloride fed to the electrolysis in step f) is in the range of from 110 to 220 g/l and/or the concentration of the alkali hydroxide solution obtained from the electrolysis in step f) is in the range of from 14 to 32% by weight.

16. The process of claim 1, wherein said at least one monophenol in step b) is of formula (I)

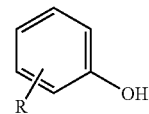

(I)

wherein R is hydrogen, halogen, or a branched or unbranched $C_1$-$C_9$-alkyl radical or alkoxycarbonyl radical.

17. The process of claim 1, wherein said at least one monophenol in step b) is selected from the group consisting of phenol, alkylphenols, and halophenols.

18. The process of claim 17, wherein said alkylphenols are selected from the group consisting of cresols, p-tert-butylphenol, p-cumylphenol, p-n-octylphenol, p-isooctylphenol, p-n-nonylphenol, and p-isononylphenol, and said halophenols are selected from the group consisting of p-chlorophenol, 2,4-dichlorophenol, p-bromophenol, and 2,4,6-tribromophenol.

19. The process of claim 17, wherein said at least one monophenol in step b) is phenol.

* * * * *